United States Patent [19]

Bader

[11] 4,284,446
[45] Aug. 18, 1981

[54] CULTURE SAMPLING DEVICE

[76] Inventor: Robert F. Bader, 1269 N. Clark St., Los Angeles, Calif. 90069

[21] Appl. No.: 120,503

[22] Filed: Feb. 11, 1980

Related U.S. Application Data

[62] Division of Ser. No. 23,790, Mar. 26, 1979.

[51] Int. Cl.³ .................... B29C 27/14; A61B 10/00; B32B 1/08
[52] U.S. Cl. ........................ 156/69; 53/425; 128/750; 128/759; 156/289; 156/290; 156/294; 156/227; 422/1; 428/35; 428/36
[58] Field of Search ............... 156/69, 294, 289, 290, 156/227; 428/35, 36; 53/425; 422/1

[56] References Cited

U.S. PATENT DOCUMENTS

| | | | |
|---|---|---|---|
| 2,902,146 | 9/1959 | Doherty | 128/759 X |
| 3,017,879 | 1/1962 | Sapit et al. | 128/636 |
| 3,037,496 | 6/1962 | Melges | 128/738 X |
| 3,168,092 | 2/1965 | Silverman | 128/759 X |
| 3,394,699 | 7/1968 | Koett | 128/759 |
| 3,433,214 | 3/1969 | Silverman | 128/759 X |
| 3,438,366 | 4/1969 | Kariher et al. | 128/757 |
| 3,513,830 | 5/1970 | Kalayjian | 128/759 |
| 3,525,329 | 8/1970 | Zeimer | 128/749 X |
| 3,669,099 | 6/1972 | Silverman | 128/768 |
| 3,839,841 | 10/1974 | Amplatz | 53/425 |
| 3,884,011 | 5/1975 | Patton | 53/425 X |
| 3,908,663 | 9/1975 | Viek | 128/768 |
| 3,947,310 | 3/1976 | Parker | 156/289 X |
| 4,023,559 | 5/1977 | Gaskell | 128/759 |

Primary Examiner—John T. Goolkasian
Assistant Examiner—Robert A. Dawson
Attorney, Agent, or Firm—Smyth, Pavitt, Siegemund & Martella

[57] ABSTRACT

A device for obtaining a culture sample from a particular location in a body passage while avoiding contamination of the sample by materials located elsewhere in the body passage includes a stiff flexible tube. A sleeve of pliant waterproof material surrounds the tube and the distal end of the sleeve is tucked into the distal end of the tube. A bag of pliant waterproof material is bonded to the outside surface of the sleeve to form a waterproof seal extending all around the sleeve, the bag enclosing the distal end of the tube and the distal end of the sleeve. The bag has a limited burst strength and is broken after the distal end has been emplaced at a particular pre-sampling level to expose the sterile sleeve that was tucked into the tube. As the tube is inserted a short distance further, the portion of the sleeve that was tucked into the tube everts out of the distal end of the tube to form a sterile curtain surrounding the distal end of the tube and protecting it from contamination. The sample can then be taken by sucking it up the tube or, more typically, by inserting a sampling tube of smaller diameter through the tube, injecting a wash, and withdrawing the wash through the sampling tube.

10 Claims, 16 Drawing Figures

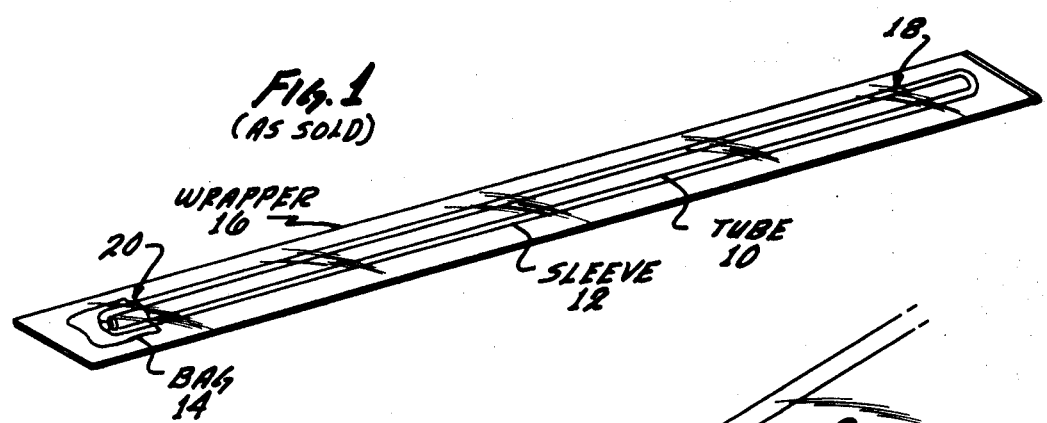
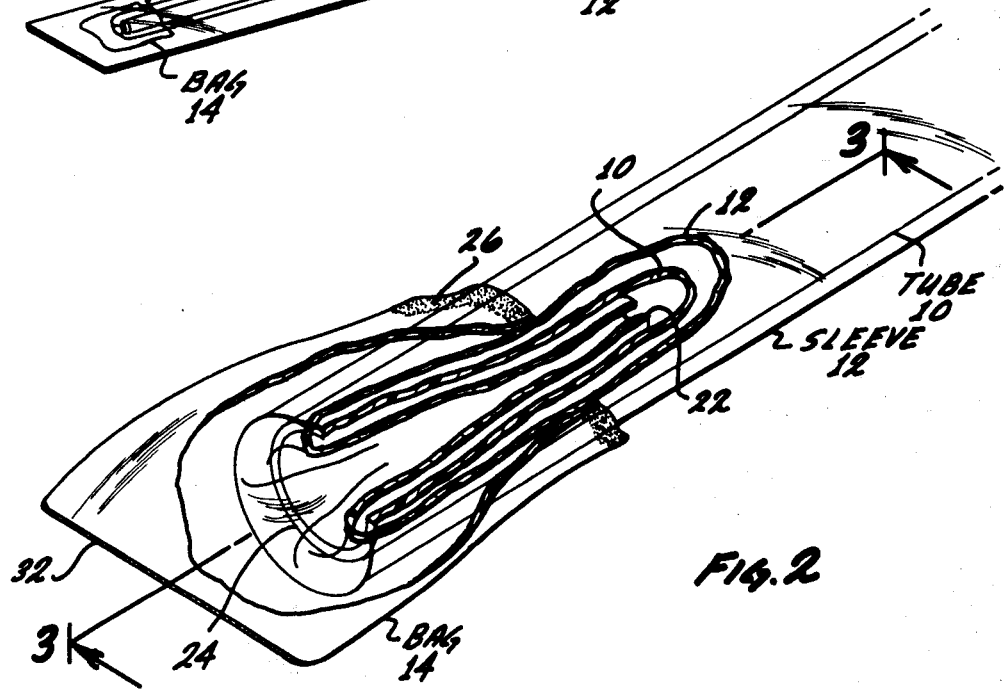
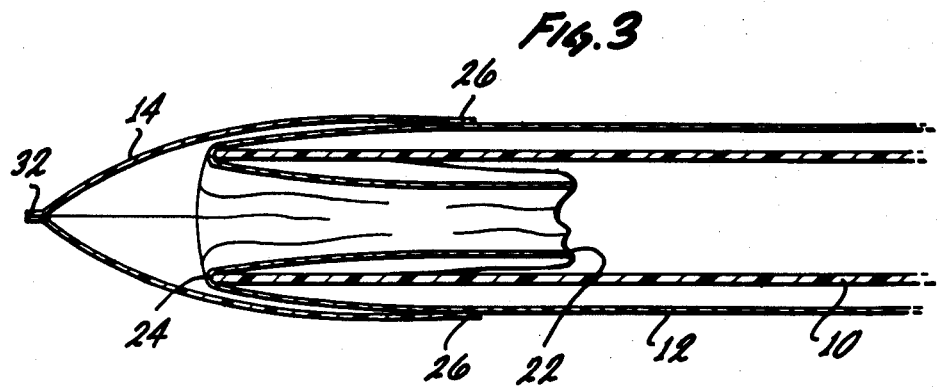

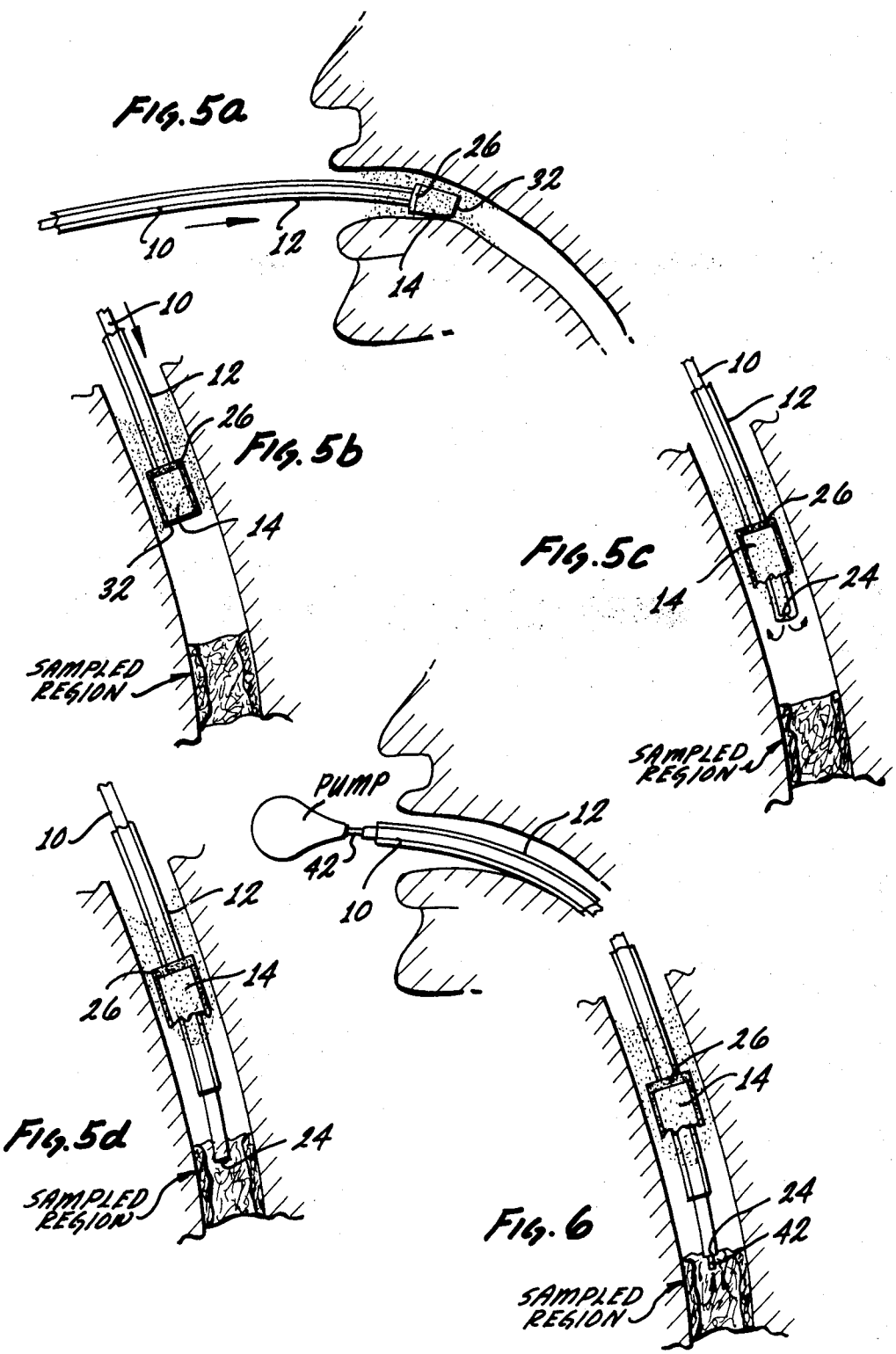

CULTURE SAMPLING DEVICE

This is a division of application Ser. No. 023,790, filed Mar. 26, 1979.

BACKGROUND OF THE INVENTION

1. Field of the Invention

The present invention is in the field of medical instruments and more particularly, relates to a device for obtaining a culture sample from a particular portion of a body passage, while avoiding contamination of the sample from other portions of the passage.

2. The Prior Art

Although the device of the present invention can be used effectively in obtaining a sample from any of several body passages, the device was developed originally in response to the need for a better way of obtaining samples from the trachea and/or bronchial areas while avoiding contamination of the sample by organisms in the mouth.

Heretofore, such samples were obtained by surgical penetration into the trachea. An incision was made in the neck of the patient and a hollow-bore needle was inserted into the trachea. Next, a catheter was passed through the hollow needle and into the trachea. Thereafter, a sample of the secretion was aspirated through the catheter. Although this procedure bypasses the patient's mouth, and avoids mouth contaminants, it was, nevertheless, a specialty procedure, relatively expensive to perform and carrying bleeding complications, discomfort to the patient, and risk of penetration to surrounding structures.

The problem of obtaining uncontaminated samples is well-known, and a number of different approaches to the problem have been suggested. The known approaches all require relatively complicated rigid structures which entail some risk of sample contamination.

In U.S. Pat. No. 3,037,496, issued June 5, 1962, Melges discloses a fertility testing apparatus, including three telescoping tubes and a rupturable closure at the distal end. Extension of the testing element beyond the contaminated distal end of the tube is limited, and accordingly, contamination of the sample at the end of the tube is possible.

In U.S. Pat. No. 3,513,830, issued May 26, 1970 to Kalayjian, there is shown an instrument for obtaining body cultures in which a tube is closed at the distal end by a cap which is opened by pushing from within the tube, and once the cap has been opened, the sample-taking surface is extended through the open distal end of the tube. Because the cap is contaminated, it is possible for the sampling swab to become contaminated as it is extended past the cap.

The devices shown in U.S. Pat. No. 3,394,699, issued July 10, 1968 to Koett and in U.S. Pat. No. 3,438,366, issued Apr. 15, 1969 to Kariher et al., employ similar arrangements at the distal end of the device for reducing contamination of the sample. In these devices, an inner rod includes a sealing knob which fits into the distal end of the tube to seal it to prevent contamination of the sample-gathering surface which is located on the central rod adjacent the knob at its end. During insertion, the knob becomes contaminated, and the same motion which exposes the sampling surface also smears the contaminated material on the knob along the area to be sampled, thereby contaminating the area.

In U.S. Pat. No. 3,017,879, issued Jan. 23, 1962 to Sapit et al., there is shown a fertility tester in which the sampling tip is extended through a hole at the end of the tube after the tube has been put in place. This device, like the Melges device discussed above, has no provision for preventing contamination of the sampling material by the contaminated distal end of the tube.

In U.S. Pat. No. 4,023,559, issued May 17, 1977 to Gaskell there is shown a sampling device in which the swab is surrounded by two telescoped tubes. After the device has been placed in position, the inner tube which encloses the swab is pushed through the distal end of the outer tube which has been cut to form segments which normally close the end of the outer tube, but which are resiliently displaceable by the inner tube. The inner tube is then extended through the distal end of the outer tube, and finally, the swab is extended beyond the distal end of the inner tube. Although this device is an improvement over previous devices, there is still a reduced risk of contamination. The device must necessarily be relatively rigid, and therefore may not be suitable for use in certain body passages.

Thus, the amount of effort expended by previous workers in the field indicates the importance of the problem and suggests that the ideal solution has not yet been found.

SUMMARY OF THE INVENTION

The present invention avoids surgical penetration into the body passage, such as the trachea, to obtain an uncontaminated sample. Compared to the devices described above, the present invention significantly reduces contamination of the sample. The structure of the device of the present invention is more flexible than other devices known in the art and it can be produced less expensively. Use of the device of the present invention is relatively simple.

In accordance with the present invention, a sterile sleeve everts from the distal end of a tube that has been inserted into a body passage thereby providing a sterile curtain surrounding the tube and protecting it from contamination from the outer portions of the device.

In accordance with the present invention, the device includes a stiff flexible tube which is surrounded by a pliable sleeve of plastic film. The distal end of the sleeve is tucked into the distal end of the tube. Thereafter, a pliable bag of plastic film is bonded to the outer surface of the sleeve near its distal end so that the bag protects the distal end of the tube from contamination as the distal end is passed through the body passage. Once the distal end of the tube has nearly reached the desired sampling location, the protective bag is broken and as the tube is further inserted, the portion of the sleeve that had been tucked into the tube everts to provide a sterile protective curtain spaced along the interior of the passage between the contaminated bag and the sterile tip of the tube.

Once the tube has thus been deployed, the sample may be captured by applying suction to the proximal end of the tube, by inserting a swab through the tube to the area to be sampled, or by inserting a sampling tube through the deployed tube, injecting a wash through the sampling tube, and then withdrawing the culture-bearing wash through the sampling tube. The most appropriate one of these three sampling techniques would be chosen with regard to the specific medical situation presented.

It is seen that the device of the present invention includes only one stiff part, namely the tube. The other parts are constructed of a plastic film in a preferred embodiment. This construction serves to distinguish the present invention from devices known to the art and results in a device which is simple and inexpensive to manufacture. Thus, it is contemplated that the device would be disposed of following its use.

The novel features, which are believed to be characteristic of the invention, both as to its structure, its method of manufacture, and its method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description and are not intended as a definition of the limits of the invention.

BRIEF DESCRIPTION OF THE DRAWINGS

FIG. 1 is a perspective view of the culture sampling device of the present invention as it will be sold;

FIG. 2 is a perspective view of the distal end of the culture sampling device;

FIG. 3 is a cross sectional view of the device of FIG. 2 in the direction 3—3 indicated in FIG. 2;

FIGS. 5a-5d are diagrams illustrating successive stages in the emplacement of the culture sampling device; and, FIG. 6 is a diagram illustrating the taking of a sample by means of the device.

DETAILED DESCRIPTION OF THE PREFERRED EMBODIMENT

Figure 4A:
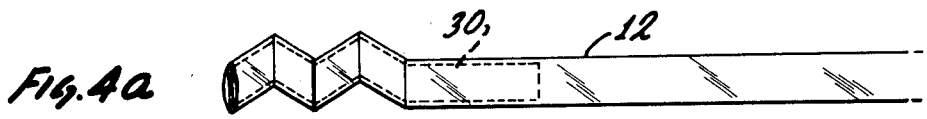
FIGS. 4a-4h are side views showing the culture sampling device of the present invention at various successive stages of its assembly.
Figure 4B:

Turning now to the drawings in which like parts are denoted by the same reference numeral throughout, there is shown in FIG. 1 the culture sampling device of the present invention as it would be packaged for sale. The device is seen to include a tube 10, a sleeve 12 and a bag 14. The sampling device will be packaged in a wrapper 16 when sold, the wrapper 16 serving to maintain its contents in a clean, but not necessarily sterile, condition. The culture sampling device includes a proximal end 18 and a distal end 20.

The perspective view of FIG. 2 shows the distal end 20 of the culture sampling device in greater detail, the device being cut away to reveal the structure more clearly. It is seen that the sleeve 12 surrounds the tube 10 and that the distal end 22 of the sleeve is tucked into the distal end 24 of the tube. The bag 14 surrounds the distal end 24 of the tube as well as the portion of the sleeve which surrounds the distal end 24 of the tube. The bag 14 is bonded to the sleeve 12 in a bond 26 which extends completely around the sleeve 12. FIG. 3 is a cross-sectional view in the direction 3—3 shown in FIG. 2.

As shown in FIGS. 2 and 3, the bag 14 provides an enclosure for the distal end 24 of the tube and for the portion of the sleeve 12 which extends distally from the bond 26.

In a preferred embodiment of the culture sampling device for use in obtaining a virgin sample of lower airway material for bacteriologic study, the tube 10 consists of Teflon, although polyethylene could be used. The tube measures approximately 38 cm in length and has an outer diameter of 6 mm and an inside diameter of 5 mm; the tube 10 is thus flexible but not pliant.

In the same preferred embodiment, the sleeve 12 consists of a thin film of pliable polyethylene approximately 43 cm in length. The bag 14 also consists of a thin film of polyethylene approximately 1.5 mils thick and roughly 18 mm across its distal end.

For reasons which will become clear later, it is important that the distal end 24 of the tube 10 have a smooth finish, and in various embodiments, the distal end 24 of the tube is rounded, beaded, or slightly flanged outwardly. Because the material of which the tube 10 is formed is normally supplied in long coils, the blunting and/or smoothing of the distal end 24 of the tube is preferably accomplished by forcing the distal end against an extremely hot flat surface or mandrel.

FIGS. 4a-4h are diagrams illustrating successive stages in fabricating the culture sampling device. As shown in FIG. 4a, a tubular piece of polyethylene film is cut to a length of approximately 38 cm to provide the sleeve 12, and a paper-like sheet of Teflon-coated fiberglass cloth in the form of a strip 30 is inserted into the distal end of the sleeve. The distal end of the sleeve is then accordion-folded as indicated in FIG. 4a to produce the configuration shown in FIG. 4b. A clip is used to hold the folded sleeve in the configuration shown in FIG. 4b.

Figure 4C:
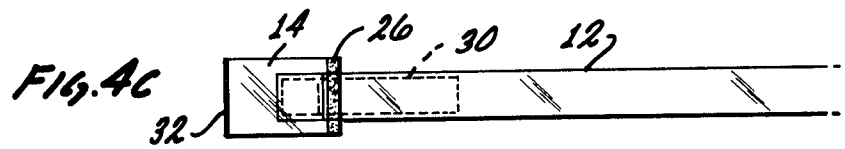
Figure 4D:
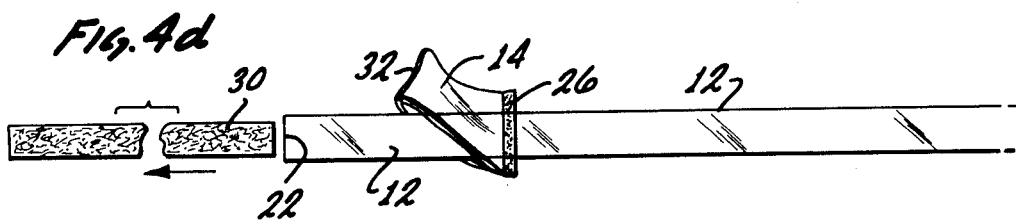

Next, the bag 14 is partially formed by superimposing two squares of 1.5 mil polyethylene film measuring approximately 5 cm square and bonding the squares together a few millimeters inside one edge to form the bond 32. It is critical that this bond break under an appropriate amount of manual force, and in the best known mode of producing the device the bond 32 is produced by the use of a Vertrod 14 WHDR thermal impulse machine, which is a pneumatically-powered high-speed thermal impulse trim sealer with blowoff. Heat and dwell are adjusted to 3½-4 and this setting is found to produce the desired results. The thus-bonded two squares of polyethylene material which will form the bag 14 are laid on a surface and the distal end of the sleeve 12 is inserted between the two sheets as shown in FIG. 4c. Next, a high-strength bond 26 is formed, joining the entire circumference of the sleeve 12 to the bag. The strip 30 prevents the opposite sides of the sleeve 12 from being bonded together, which would close the sleeve undesirably at the bond 26. At this point in the process, the bag is closed at opposite ends by the bonds 32, 26, but remains open at the sides. Next, as shown in FIG. 4d, the bag 14 is drawn to one side, the accordion-folded sleeve 12 is drawn through one of the open sides of the bag 14 and is unfolded, and the strip 30 is then withdrawn from the sleeve.

Figure 4E:
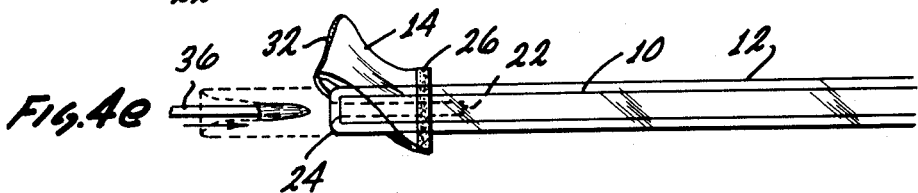
Figure 4F:
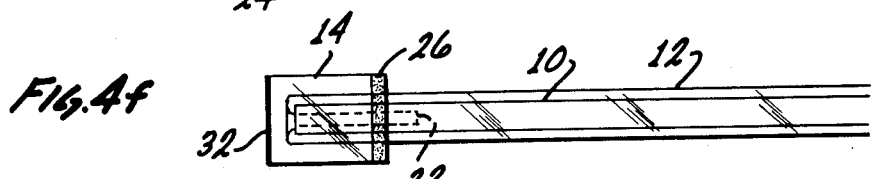
Figure 4G:
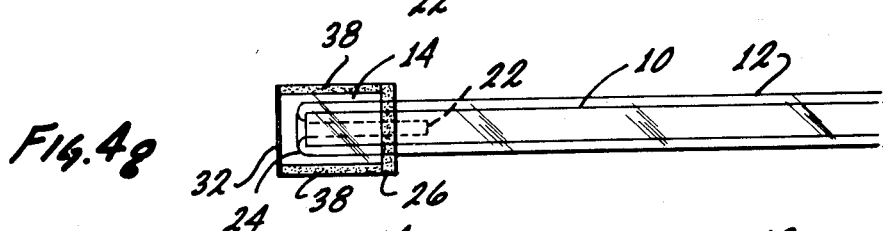
Figure 4H:
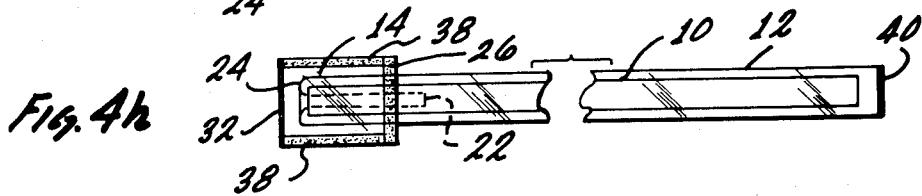

As indicated in FIG. 4e the tube 10 is next inserted into the sleeve 12, normally through the proximal end of the sleeve, and the distal end 22 of the sleeve is tucked into the distal end 24 of the tube 10 by the use of a ramrod-like tool 36, which typically is passed entirely through the tube 10 from its distal end 24 to emerge from the proximal end of the tube. After the distal end 22 of the sleeve has been tucked into the distal end 24 of the tube and after the bag 14 has been returned to its normal position, the device has the intermediate form shown in FIG. 4f. Thereafter, the sides of the bag 14 are sealed by the bonds 38 as shown in FIG. 4g, and then the proximal end of the sleeve is closed by the bond 40 as shown in FIG. 4h. Thereafter, the device of FIG. 4h may be sealed in the wrapper 16 and sterilized. In a preferred embodiment, the side bonds 38 are impressed at a slightly angle so that the final bag shape is a trapezoid in which the bond 26 is approximately 26 mm in length while the bond 32 is approximately 18 mm in length. In accordance with normal practice, excess material remaining outside the trapezoid formed by the bonds 32, 26, 38 is trimmed away.

In another embodiment, the bond 26 is produced first, then the distal end of the sleeve is tucked into the distal end of the tube and the remaining bonds are produced to close the bag. In still another embodiment the bond 32 and one of the bonds 38 are produced, then the distal end of the sleeve is tucked into the distal end of the tube, and finally bonds 26, 38 are produced.

The procedure for using the culture sampling device of the present invention is relatively simple. After routine bronchoscopic sedation, the patient is placed in a supine position with neck flexed and head extended. The device is removed from its protective wrapper 16. While the glottic opening is visualized with a standard laryngoscope, the tube is passed between the patient's vocal chords to a level of approximately two inches past the glottic opening as shown in FIG. 5b. At this stage it must be assumed that the entire exposed surface of the sleeve and the surface of the bag are covered with oral contaminant organisms, as indicated by a number of small dots in FIG. 5b.

The physician then holds the sleeve 12 stationary while forcing the tube forward, thereby rupturing the bond 32, as shown in FIG. 5c. Thereafter, the tube 10 is advanced, causing the portion of the sleeve 12 that was tucked within the distal end 24 of the tube to progressively evert from the distal end of the tube to form a progressively lengthening sterile shield isolating the extended distal end 24 of the tube from the contaminated surfaces of the bag 14 and the sleeve 12, as shown in FIG. 5d.

Once the distal end 24 of the tube has been emplaced in the region from which the sample is to be taken, as shown in FIG. 5d, the sample may be captured by any of several techniques well-known in the art. As shown in FIG. 6, a small-bore sampling tube or catheter may be inserted through the tube 10, and a wash can be injected through the sampling tube 42 to the area to be sampled. The wash is then withdrawn through the sampling tube and the entire apparatus is removed from the patient. In other circumstances, it may be practical to draw a fluid to be sampled directly through the tube 10. Also, under some circumstances it may be practical to insert through the tube 10 a sterile swab on which the sample is collected.

Thus, there has been described a culture sampling device which provides positive isolation between the portion of the device which contacts the sampled region and the contaminated portion of the device. The culture sampling device of the present invention is relatively simple in its construction and relatively inexpensive to manufacture.

The culture sampling device has been described in the context of obtaining samples from the tracheal and bronchial regions of a patient's airway. The particular utility of the invention in connection with this environment does not limit the fields in which it may be exploited. It should be clear that the culture sampling device of the present invention can be used for obtaining samples from other body passages, wherever there is risk that the sample will be contaminated by cultures in other portions of the body passage.

The foregoing detailed discription is illustrative of a preferred embodiment of the invention, but it is to be understood that additional embodiments will be obvious to those skilled in the art. The embodiments described herein together with the additional embodiments are considered to be within the scope of the invention.

What is claimed is:

1. A method of forming a culture sampling device of the type including a relatively flexible tube, a sleeve of pliant waterproof material surrounding the tube, the sleeve having a proximal end and having a distal end tucked into the distal end of the tube, and including a bag of pliant waterproof material enclosing the distal end of the tube and bonded to the outside surface of the sleeve to form a waterproof seal extending all around the sleeve, said method comprising the steps of:
   (1) bonding flaps to the outside surface of the sleeve along a line located a specified distance from the distal end of the sleeve, said line extending all around the sleeve;
   (2) positioning the tube within the sleeve with the distal end of the tube nearer the distal end of the sleeve;
   (3) tucking a portion of the sleeve adjacent the distal end of the sleeve into the distal end of the tube; and
   (4) bonding the flaps together so that together the flaps form a waterproof bag enclosing the distal end of the tube.

2. The method of claim 1 further comprising the preliminary step, before step (1), of inserting into the sleeve a strip of non-bondable material, and further comprising the step, after step (1), of removing the strip of non-bondable material from the sleeve, whereby the strip of non-bondable material prevents overlapping portions of the sleeve from becoming bonded together.

3. The method of claim 1 further comprising the step of sealing the proximal end of the sleeve to enclose the proximal end of the tube.

4. The method of claim 1 further comprising the step of sterilizing the device formed.

5. A method of forming a culture sampling device of the type including a relatively flexible tube, a sleeve of pliant waterproof material surrounding the tube, the sleeve having a proximal end and having a distal end tucked into the distal end of the tube, and including a bag of pliant waterproof material enclosing the distal end of the tube and bonded to the outside surface of the sleeve to form a waterproof seal extending all around the sleeve, said method comprising the steps of:
   (1) gathering a section of the sleeve adjacent the distal end of the sleeve;
   (2) placing the gathered section of the sleeve into a bag having an open end and having an aperture;
   (3) bonding the open end of the bag to a portion of the sleeve adjacent the gathered section so that the open end of the bag is sealed and so that a waterproof seal between the open end of the bag and the outside surface of the sleeve extends completely around the sleeve, the aperture of the bag remaining open;
   (4) positioning the tube within the sleeve with the distal end of the tube nearer the distal end of the sleeve;
   (5) tucking the gathered section of the sleeve into the distal end of the tube, working through the aperture in the bag;

(6) sealing the aperture of the bag.

6. The method of claim 5 further comprising the preliminary step, before step (3), of inserting into the sleeve a strip of non-bondable material, and further comprising the step, after step (3), of removing the strip of non-bondable material from the sleeve, whereby the strip of non-bondable material prevents overlapping portions of the sleeve from becoming bonded together.

7. The method of claim 5 further comprising the step of sealing the proximal end of the sleeve to enclose the proximal end of the tube.

8. The method of claim 5 further comprising the step of sterilizing the device formed.

9. The method of claim 5 further comprising the gathering step further comprises folding.

10. The method of claim 5 wherein the gathering step further comprises rolling.

* * * * *